United States Patent
Du et al.

(10) Patent No.: US 7,119,063 B2
(45) Date of Patent: Oct. 10, 2006

(54) MEMORY-ENHANCING PEPTIDES AND THE USE THEREOF

(75) Inventors: Yucang Du, Shanghai (CN); Jinhuan Shen, Shanghai (CN)

(73) Assignee: Shanghai Cas Intide Biotech Co., Ltd., Shanghai (CN)

( * ) Notice: Subject to any disclaimer, the term of this patent is extended or adjusted under 35 U.S.C. 154(b) by 520 days.

(21) Appl. No.: 10/311,858

(22) PCT Filed: May 28, 2001

(86) PCT No.: PCT/CN01/00875

§ 371 (c)(1),
(2), (4) Date: Dec. 20, 2002

(87) PCT Pub. No.: WO02/02592

PCT Pub. Date: Jan. 10, 2002

(65) Prior Publication Data

US 2004/0116656 A1 Jun. 17, 2004

(30) Foreign Application Priority Data

Jun. 30, 2000 (CN) ............................ 00 1 16876

(51) Int. Cl.
*A01N 37/18* (2006.01)
(52) U.S. Cl. .......................................... 514/2
(58) Field of Classification Search ............. None
See application file for complete search history.

(56) References Cited

U.S. PATENT DOCUMENTS 4,487,765 A * 12/1984 de Wied .................. 514/15
4,623,640 A * 11/1986 de Wied .................. 514/18

OTHER PUBLICATIONS

J-Lee., etal, 1995, Bull. Korean. Chem. Soc., 16, 591-594.*
Chang C-D, 1980, Int. J. Peptide Protein Res., 15, 59-66.*
Wunsch E., 1982, Hoppe-Seyler's Z. Physio. Chem., 363, 1461-1464.*
Luo P., 1999, Proc. Natl. Acad. Sci., 96, 4930-5.*
Creamer, T. P., etal., 1992, Proc. Natl. Acad. Sci., 89, 5937-5941.*
J-S Lee, et al., 1995, and Bull. Korean. Chem. Soc., 16, 591-594.*

* cited by examiner

Primary Examiner—Bruce R. Campell
Assistant Examiner—Satyanarayana R. Gudibande
(74) Attorney, Agent, or Firm—Rabin & Berdo, P.C.

(57) ABSTRACT

In this invention, chemical synthesis method has been used to improve the structure of memory-enhancing peptide. The animal experiments demonstrated that this kind of chemicals shows remarkable physiological activities, which may be helpful in ameliorating mental impediment in adults and promoting the intelligence development in adolescent, even can be a clinical medicine for the patient of Alzheimer's disease.

15 Claims, No Drawings

SEQUENCE LISTING

<160> NUMBER OF SEQ ID NOS: 16

<210> SEQ ID NO 1
<211> LENGTH: 4
<212> TYPE: PRT
<213> ORGANISM: Artificial Sequence
<220> FEATURE:
<223> OTHER INFORMATION: Peptide Fragments

<400> SEQUENCE: 1

Asn  Ala  Pro  Arg

<210> SEQ ID NO 2
<211> LENGTH: 4
<212> TYPE: PRT
<213> ORGANISM: Artificial Sequence
<220> FEATURE:
<223> OTHER INFORMATION: Peptide Fragments

<400> SEQUENCE: 2

Asn  Leu  Pro  Arg

<210> SEQ ID NO 3
<211> LENGTH: 4
<212> TYPE: PRT
<213> ORGANISM: Artificial Sequence
<220> FEATURE:
<223> OTHER INFORMATION: Peptide Fragments

<400> SEQUENCE: 3

Asn  Ile  Pro  Arg

```
<210> SEQ ID NO 4
<211> LENGTH: 4
<212> TYPE: PRT
<213> ORGANISM: Artificial Sequence
<220> FEATURE:
<223> OTHER INFORMATION: Peptide Fragments

<400> SEQUENCE: 4

Asn Phe Pro Arg

<210> SEQ ID NO 5
<211> LENGTH: 4
<212> TYPE: PRT
<213> ORGANISM: Artificial Sequence
<220> FEATURE:
<223> OTHER INFORMATION: Peptide Fragments

<400> SEQUENCE: 5

Asn Tyr Pro Arg

<210> SEQ ID NO 6
<211> LENGTH: 4
<212> TYPE: PRT
<213> ORGANISM: Artificial Sequence
<220> FEATURE:
<223> OTHER INFORMATION: Peptide Fragments

<400> SEQUENCE: 6

Asn Val Pro Arg

<210> SEQ ID NO 7
<211> LENGTH: 4
<212> TYPE: PRT
<213> ORGANISM: Artificial Sequence
<220> FEATURE:
<223> OTHER INFORMATION: Peptide Fragments

<400> SEQUENCE: 7

Asn Cys Pro Arg

<210> SEQ ID NO 8
<211> LENGTH: 4
<212> TYPE: PRT
<213> ORGANISM: Artificial Sequence
<220> FEATURE:
<223> OTHER INFORMATION: Peptide Fragments

<400> SEQUENCE: 8

Asn Cys Pro Arg

<210> SEQ ID NO 9
<211> LENGTH: 4
<212> TYPE: PRT
<213> ORGANISM: Artificial Sequence
<220> FEATURE:
<223> OTHER INFORMATION: Peptide Fragments

<400> SEQUENCE: 9

Asn Ala Pro Arg

<210> SEQ ID NO 10
<211> LENGTH: 4
<212> TYPE: PRT
<213> ORGANISM: Artificial Sequence
<220> FEATURE:
<223> OTHER INFORMATION: Peptide Fragments
```

```
<400> SEQUENCE: 10

Asn  Leu  Pro  Arg

<210> SEQ ID NO 11
<211> LENGTH: 4
<212> TYPE: PRT
<213> ORGANISM: Artificial Sequence
<220> FEATURE:
<223> OTHER INFORMATION: Peptide Fragments

<400> SEQUENCE: 11

Asn  Ile  Pro  Arg

<210> SEQ ID NO 12
<211> LENGTH: 4
<212> TYPE: PRT
<213> ORGANISM: Artificial Sequence
<220> FEATURE:
<223> OTHER INFORMATION: Peptide Fragments

<400> SEQUENCE: 12

Asn  Phe  Pro  Arg

<210> SEQ ID NO 13
<211> LENGTH: 4
<212> TYPE: PRT
<213> ORGANISM: Artificial Sequence
<220> FEATURE:
<223> OTHER INFORMATION: Peptide Fragments

<400> SEQUENCE: 13

Asn  Tyr  Pro  Arg

<210> SEQ ID NO 14
<211> LENGTH: 4
<212> TYPE: PRT
<213> ORGANISM: Artificial Sequence
<220> FEATURE:
<223> OTHER INFORMATION: Peptide Fragments

<400> SEQUENCE: 14

Asn  Val  Pro  Arg

<210> SEQ ID NO 15
<211> LENGTH: 4
<212> TYPE: PRT
<213> ORGANISM: Artificial Sequence
<220> FEATURE:
<223> OTHER INFORMATION: Peptide Fragments

<400> SEQUENCE: 15

Asn  Cys  Pro  Arg

<210> SEQ ID NO 16
<211> LENGTH: 4
<212> TYPE: PRT
<213> ORGANISM: Artificial Sequence
<220> FEATURE:
<223> OTHER INFORMATION: Peptide Fragments

<400> SEQUENCE: 16

Asn  Cys  Pro  Arg
```

MEMORY-ENHANCING PEPTIDES AND THE USE THEREOF

FIELD OF THE INVENTION

This invention relates to a synthesis of peptide and its analogs. Particularly, it focuses on the synthesis and application.

BACKGROUND OF THE INVENTION

It has been reported that arginine-vasopressin (AVP) have effect on the memory of animals but not show obvious influence on the learning process. Since AVP is a kind of hormone in vivo and its main function is in anti-diuretic process and to enhance blood pressure, it's not appropriate for the clinical therapy in enhancing memory. Therefore, on the basis of patent "memory-enhancing peptide and its application" (Chinese Patent No. ZL 93112493.X), we go on with work about the structural improvement and perform a series of pharmacological experiments, aiming to modify the defect in the existing patent and search for new memory-enhancing peptides which have simpler structure, stronger pharmacological activity, easy to produce, and have clinically curative effect on promoting the intelligence development in adolescent, ameliorating mental impediment in adults, accelerating the memory.

SUMMARY OF THE INVENTION

The purpose of the invention is to provide for a kind of memory-enhancing peptides which can ameliorate mental impediment in adults and promote the intelligence development in adolescent, even can be a clinical medicine for the patient of Alzheimer's disease. The peptides can be incorporated into medicines and health foods.

Depending on the results of biological activity, we have designed a series of new chemicals with memory- and learning-enhancing function Their structure general formula is as following:

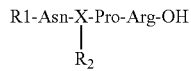

X can be Ala; Leu; Ile; Cys; Phe; Tyr; Val;

$R_1$ represents PyroGlu; H;

$R_2$ can be S—S—C—C($CH_3$)$_3$; S—C($CH_3$)$_3$; $R_2$ is a kind of hydrophobic side-chain to stabilize spatial conformation of the whole molecule.

If $R_1$ is PyroGlu, $R_2$ is S—S—C($CH_3$)$_3$ or S—C($CH_3$)$_3$ or other groups which have hydrophobic side-chain to stabilize the spatial conformation of the whole molecule.

If $R_1$ is H, $R_2$ must be S—S—C($CH_3$)$_3$ or S—C($CH_3$)$_3$ or other groups which have hydrophobic side-chain to stabilize the spatial conformation of the whole molecule.

X can be Ala; Leu; Ile; Cys; Phe; Tyr; Val.

The peptides in this invention can be obtained through solid or liquid peptide synthesis method step by step. The synthesize protocol is as following:

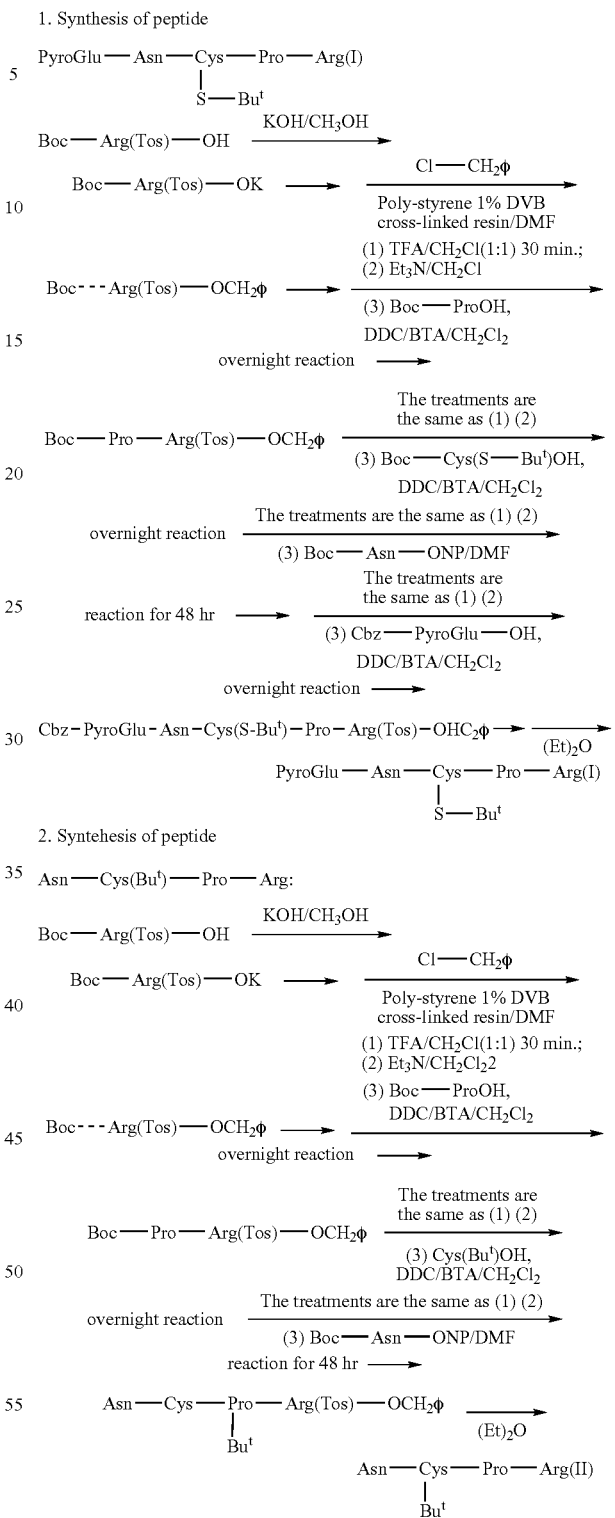

The pharmacological tests of memory-enhancing peptide in this invention have been performed as following: the animals have been divided into three groups: drug administration group, control group and model group, with each group administrated with memory-enhancing peptide, saline and scopolamine respectively. In the test, the groups except control group were injected with scopolamine after the administration of medicine about 50 min., 10 min. later, the training began. First, the animals will be put into reaction box for 3 min. before each trails to familiarize them with the environment. Then, the reaction box are charged with 36V alternating current. When the animal subjects to electrical shock, it will jump up to the central platform to avoid harmful stimulation as a normal response. Most of animals may be return to the copper curdles twice or even more times, but they will jump back to the platform swiftly as the results of electrical shock. Each test trail will be performed for 5 min. and two following indices will be used to represent the learning results: (I) the number of total error (EN) during the whole training period; (2) the reaction time (RT) for the first returning to the copper curdle in the trail. The trails will repeat again 24 hrs later as memory test. The results as shown in Table 1 demonstrated that memory-enhancing peptide can remarkably ameliorate the memory and learning impediment induced by scopolamine.

Compared with model group, the memory-enhancing peptide at the dose of 0.5 μg and 1 μg/kg can obviously improve the memory and learning impediment induced by scopolamine, shown as longer incubation period and lesser error numbers which have marked difference from those of model group($P<0.01$). In addition, memory-enhancing peptide (0.5 μg/kg and 1 μg/kg ) have better effects than Huperzine A (100 μg/kg ) in ameliorate the memory and learning impediment induced by scopolamine.

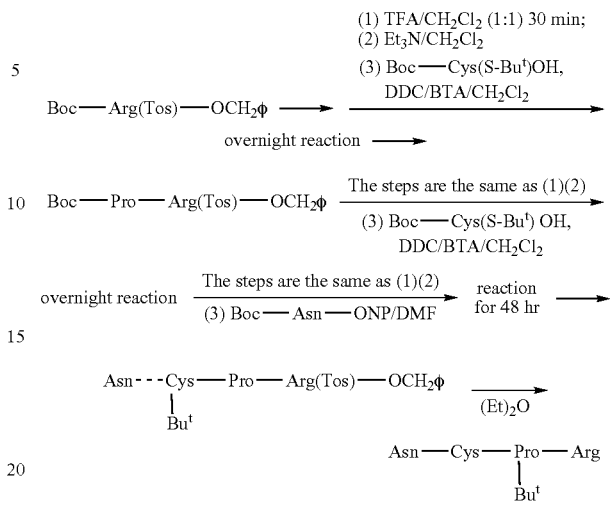

The crude product described above was separated and purified through Silica gel column (Silicagel 60) initially and then subjected to $C_{18}$ HPLC for further purification. The elution time in HPLC is 19.1 min and solution system is TFA/acetonitrile system.

TABLE 1

The effect of memory-enhancing peptide (MEP531) on the learning and memory process of mouse

| Group | Drug dosage μg/kg | Scopolamine mg/kg | Learning RT(s) | Results EN | Memory RT(s) | Results EN |
|---|---|---|---|---|---|---|
| Control group | Saline | — | 131.4 ± 98.3 | 0.9 ± 0.87 | 285.4 ± 22.6 | 0.4 ± 0.51 |
| Model group | Saline | 1 | 27.5 ± 29.4♦♦ | 2.3 ± 1.4♦ | 140 ± 117♦♦ | 1.9 ± 1.2♦♦ |
| Huperzine A | 100 | 1 | 120.5 ± 114.9* | 1.3 ± 2.3** | 231.9 ± 78** | 0.9 ± 0.7** |
| MEP-531 | 0.25 | 1 | 78.8 ± 118.7 | 0.3 ± 0.48** | 197.6 ± 75.1 | 0.9 ± 0.56** |
| MEP-531 | 0.5 | 1 | 241.6 ± 51.9** | 0.2 ± 0.4** | 245.5 ± 62.9** | 0.5 ± 0.5** |
| MEP-531 | 1 | 1 | 267.6 ± 31.4** | 0.3 ± 0.5** | 282.8 ± 33.4** | 0.3 ± 0.5** |

♦<0.05,
♦♦<0.01, compared with control group;
*<0.05,
**<0.01, compared with the model group;

DETAILED DESCRIPTION OF THE INVENTION

Implement Case 1

Chemical synthesis of Asn-Cys(Bu$^t$)-Pro-Arg(MEP422)

Boc-system step-by-step solid phase synthesis method; Started from 2 g Merrifield resin.

First,

Boc—Arg(Tos)—OH $\xrightarrow{\text{KOH/CH}_2\text{OH}}$

Boc—Arg(Tos)—OK $\xrightarrow{\text{Cl—CH}_2\phi}{\text{Poly-styrene 1\% DVB cross-linked resin/DMF}}$ The results shown in the following table demonstrated the product has reasonable amino acid component.

| Experimental value | Asn: 1.05 | Arg: 0.96 | Pro: 1.08 | Cys: not anlysis |
|---|---|---|---|---|
| Theory value | Asn: 1.00 | Arg: 1.00 | Pro: 1.00 | |
| MS analysis: | MW$^+$ 544.3 | | | |

The method described in the upper phase can also be applied to the synthesis of other analogs as X represents Ala; Leu; Ile; Phe; Tyr; Val respectively.

Implement Case 2

Chemical synthesis of PyroGlu-Asn-Cys(S-Bu$^t$)-Pro-Arg (MEP531):

Boc-system step-by-step solid phase synthesis method; Started from 2 g Merrifield resin.

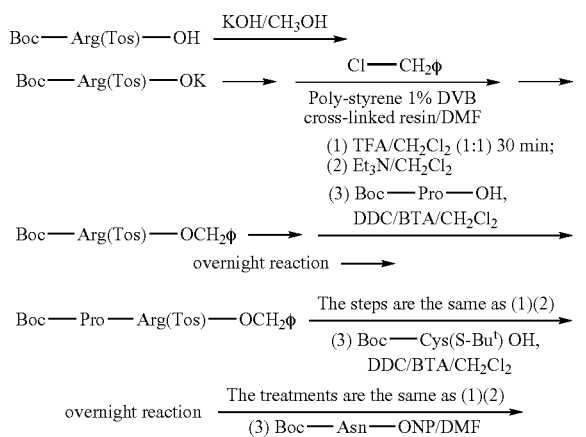

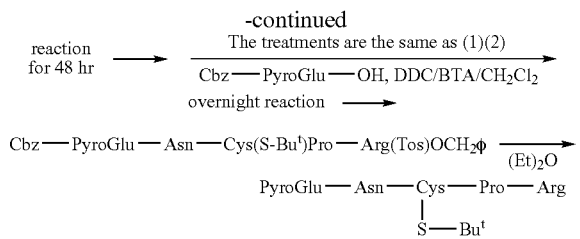

The upper crude penta-peptide preparation was separated and purified through Silica gel column initially and then subjected to $C_{18}$ HPLC for further purification. The elution time in HPLC is 19.5 min and solution system is TFA/acetonitrile system. The results shown in the following table demonstrated the products has reasonable amino acid component.

| Experimental value | Asn: 1.01 | Glu: 1.03 | Arg: 0.96 | Pro: 0.95 | Cys: not anlysis |
|---|---|---|---|---|---|
| Theory value | Asn: 1.00 | Glu: 1.00 | Arg: 1.00 | Pro: 1.00 | |
| MS analysis: | $MW^+$ 687 | | | | |

The method described in the upper phase also can be applied to the synthesis of other analogs as X represents Ala; Leu; Ile; Phe; Tyr; Val respectively.

We claim:

1. A medicine or health food comprising a memory-enhancing peptide of the formula: $R_1$-Asn-X($R_2$)-Pro-Arg-OH wherein,
X is taken from the group Ala, Leu, Ile, Cys, Phe, Tyr or Val;
$R_1$ is taken from the group PyroGlu or H; and
$R_2$ is taken from the group S—S—C($CH_3$)$_3$ or S—C($CH_3$)$_3$.

2. A medicine or health food comprising a memory-enhancing peptide according to claim 1 wherein, $R_1$ is PyroGlo.

3. A medicine or health food comprising a memory-enhancing peptide according to claim 1 wherein, $R_1$ is H.

4. A medicine or health food comprising a memory-enhancing peptide according to claim 1 wherein, $R_2$ is S—S—C($CH_3$)$_3$.

5. A medicine or health food comprising a memory-enhancing peptide according to claim 1 wherein, $R_2$ is S—C($CH_3$)$_3$.

6. A method for improving memory comprising incorporating into medicines and health foods a memory-enhancing peptide of the formula:
$R_1$-Asn-X($R_2$)-Pro-Arg-OH wherein,
X is taken from the group Ala, Leu, Ile, Cys, Phe, Tyr or Val;
$R_1$ is taken from the group PyroGlu or H; and
$R_2$ is taken from the group S—S—C($CH_3$)$_3$ or S—C($CH_3$)$_3$.

7. A method for ameliorating memory impediments and improving intelligence in juveniles by administering to said juveniles a memory enhancing peptide of the formula:
$R_1$-Asn-X($R_2$)-Pro-Arg-OH
wherein,
X is taken from the group Ala, Leu, Iie, Cys, Phe, Tyr, or Val;
$R_1$ is taken from the group PyroGlu or H; and
$R_2$ is taken from the group S—S—C($CH_3$)$_3$ or S—C($CH_3$)$_3$.

8. The method of claim 6 wherein $R_1$ of said memory enhancing peptide is PyroGlu.

9. The method of claim 6 wherein $R_1$ of said memory enhancing peptide is H.

10. The method of claim 6 wherein $R_2$ of said memory enhancing peptide is S—S—C($CH_3$)$_3$.

11. The method of claim 6 wherein $R_2$ of said memory-enhancing peptide is S—C($CH_3$)$_3$.

12. The method of claim 7 wherein $R_1$ of said memory enhancing peptide is PyroGlu.

13. The method of claim 7 wherein $R_1$ of said memory enhancing peptide is H.

14. The method of claim 7 wherein $R_2$ of said memory enhancing peptide is S—S—C($CH_3$)$_3$.

15. The method of claim 7 wherein $R_2$ of said memory-enhancing peptide is S—C($CH_3$)$_3$.

* * * * *

UNITED STATES PATENT AND TRADEMARK OFFICE
CERTIFICATE OF CORRECTION

| | |
|---|---|
| PATENT NO. | : 7,119,063 B2 |
| APPLICATION NO. | : 10/311858 |
| DATED | : October 10, 2006 |
| INVENTOR(S) | : Yucang Du et al. |

It is certified that error appears in the above-identified patent and that said Letters Patent is hereby corrected as shown below:

Column 11, line 12, change "PyroGlo" to --PyroGlu--.

Signed and Sealed this

Ninth Day of January, 2007

JON W. DUDAS
*Director of the United States Patent and Trademark Office*